United States Patent
Ramirez (12)

(10) Patent No.: US 10,245,344 B2
(45) Date of Patent: Apr. 2, 2019

(54) DEODORIZING CATCH TRAY FOR HAND DRYERS

(71) Applicant: Edgardo Ramirez, Livermore, CA (US)

(72) Inventor: Edgardo Ramirez, Livermore, CA (US)

(*) Notice: Subject to any disclaimer, the term of this patent is extended or adjusted under 35 U.S.C. 154(b) by 215 days.

(21) Appl. No.: 15/336,638

(22) Filed: Oct. 27, 2016

(65) Prior Publication Data
US 2018/0117207 A1 May 3, 2018

(51) Int. Cl.
| | |
|---|---|
| *B65G 59/00* | (2006.01) |
| *A47K 10/24* | (2006.01) |
| *A24F 27/14* | (2006.01) |
| *A61L 9/12* | (2006.01) |
| *A47K 10/48* | (2006.01) |

(52) U.S. Cl.
CPC .......... *A61L 9/122* (2013.01); *A61L 9/12* (2013.01); *A47K 10/48* (2013.01); *A61L 2209/13* (2013.01); *A61L 2209/21* (2013.01)

(58) Field of Classification Search
CPC .. A61L 9/122; A61L 2209/13; A61L 2209/21; A47K 10/48
USPC ........ 422/5, 28; 34/201–202, 218, 523, 554; 221/1, 135, 45
See application file for complete search history.

(56) References Cited

FOREIGN PATENT DOCUMENTS

DE 10 2006 019 658 * 10/2007 ............. A47K 10/48

OTHER PUBLICATIONS

European Patent Office English Translation of the Claims Section of DE 10 2006 019 658 A1 (Year: 2007).*
European Patent Office English Translation of the Description Section of DE 10 2006 019 658 A1 (Year: 2007).*
European Patent Office English Translation of the Drawings Section of DE 10 2006 019 658 A1 (Year: 2007).*
Applicant Admitted Prior Art (Specification, p. 1, [0003].*

* cited by examiner

*Primary Examiner* — Monzer R Chorbaji
(74) *Attorney, Agent, or Firm* — Clements Bernard Walker PLLC; Jeffrey S. Bernard

(57) ABSTRACT

Some embodiments of the present disclosure include a device for catching water under a hand dryer while simultaneously deodorizing a surrounding area. The device may include a stand-alone catch tray; and a deodorizing screen positioned within the catch tray such that forced air from the hand dryer contacts the deodorizing screen when the hand dryer is in use causing the deodorizing screen to release a fragrance and deodorize a surround area. The catch tray may include a top tray including a recessed sponge compartment sized to accommodate a sponge; a sponge positioned within the recessed sponge compartment; a base tray attached to the top tray; and a back wall extending upward from the base tray.

6 Claims, 3 Drawing Sheets

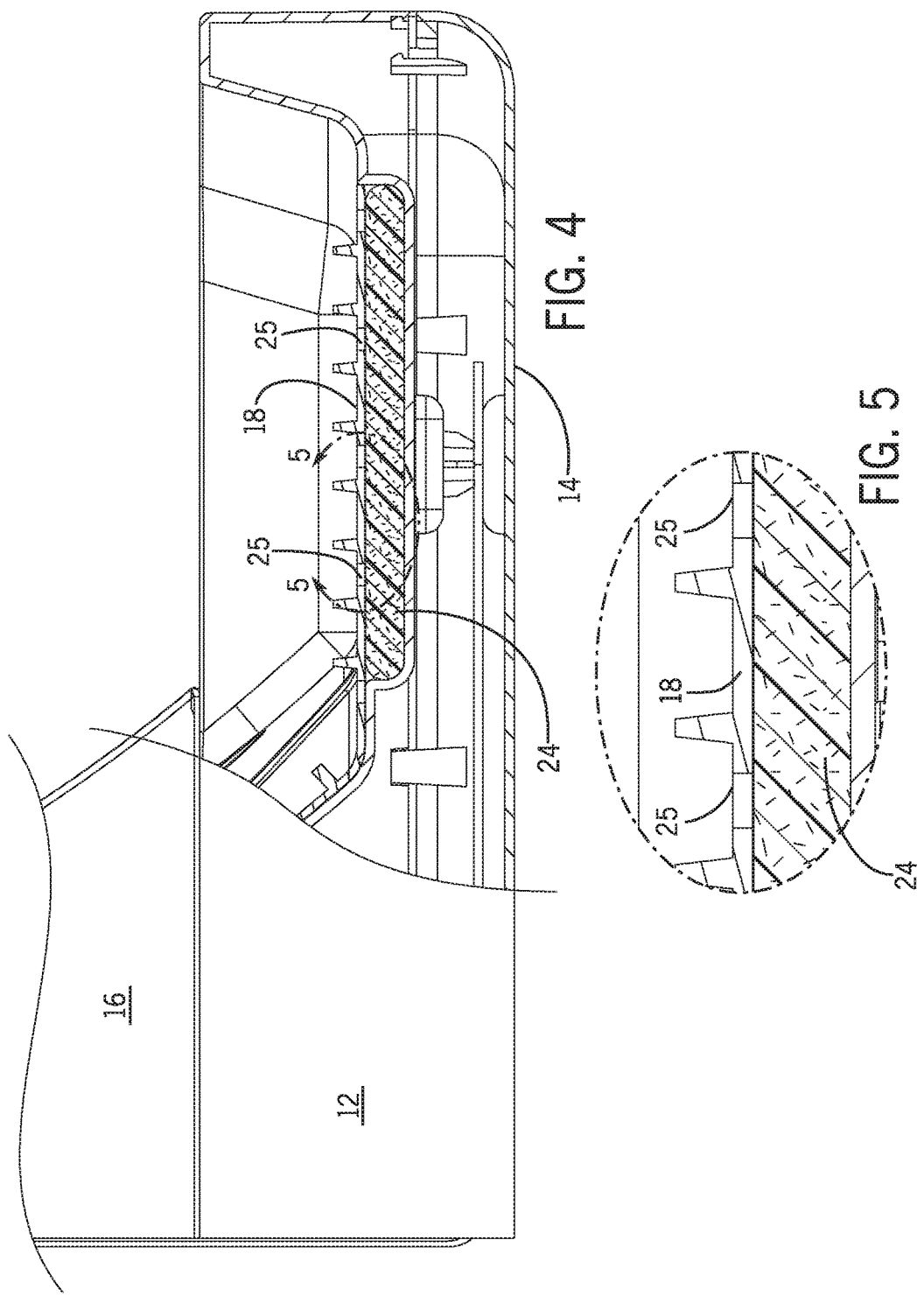

DEODORIZING CATCH TRAY FOR HAND DRYERS

BACKGROUND

The embodiments herein relate generally to hand dryers, and more particularly, to a deodorizing catch tray for hand dryers.

Use of hand dryers, such as those in public restrooms, causes water to drip down the wall under the hand dryer, getting the floor wet and messy. This problem is not only unsanitary, but also damages the floor and walls, creating additional cleaning and costs for the maintenance of the facility. Additionally, all public restrooms suffer from bad odors, which can be difficult to mask with sprays or deodorants due to a lack of movement of air.

Some conventional hand dryers include built-in catch trays. However, there is no stand-alone catch system that can be adapted for use with all hand dryers that do not have a built in tray. Moreover, none of the existing hand dryers have built-in deodorizers. Rather, restrooms are often deodorized by manual or automatic sprays.

Therefore, what is needed is a combination catch tray and deodorizer configured to be used with any existing hand dryer.

SUMMARY

Some embodiments of the present disclosure include a device for catching water under a hand dryer while simultaneously deodorizing a surrounding area. The device may include a stand-alone catch tray; and a deodorizing screen positioned within the catch tray such that forced air from the hand dryer contacts the deodorizing screen when the hand dryer is in use causing the deodorizing screen to release a fragrance and deodorize a surround area. The catch tray may include a top tray including a recessed sponge compartment sized to accommodate a sponge; a sponge positioned within the recessed sponge compartment; a base tray attached to the top tray; and a back wall extending upward from the base tray

BRIEF DESCRIPTION OF THE FIGURES

The detailed description of some embodiments of the invention is made below with reference to the accompanying figures, wherein like numerals represent corresponding parts of the figures.

FIG. 4 is a side elevation view of one embodiment of the present disclosure.

FIG. 5 is a detail cross-sectional view of one embodiment of the present disclosure, taken along line 5-5 in FIG. 4.

DETAILED DESCRIPTION OF CERTAIN EMBODIMENTS

Figure 1:
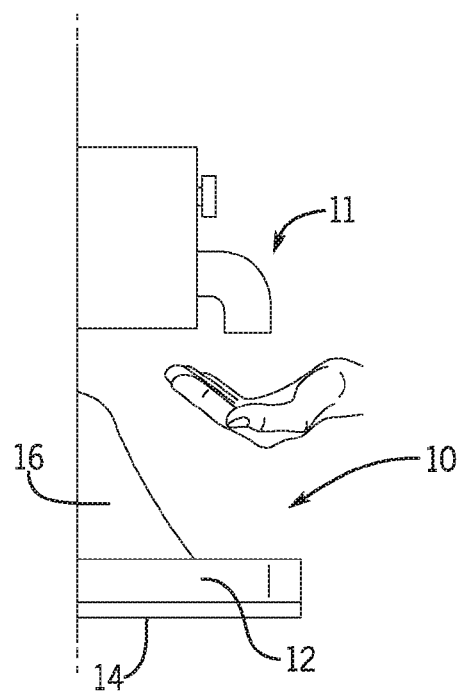
FIG. 1 is side elevation view of one embodiment of the present disclosure, shown in use.
Figure 2:
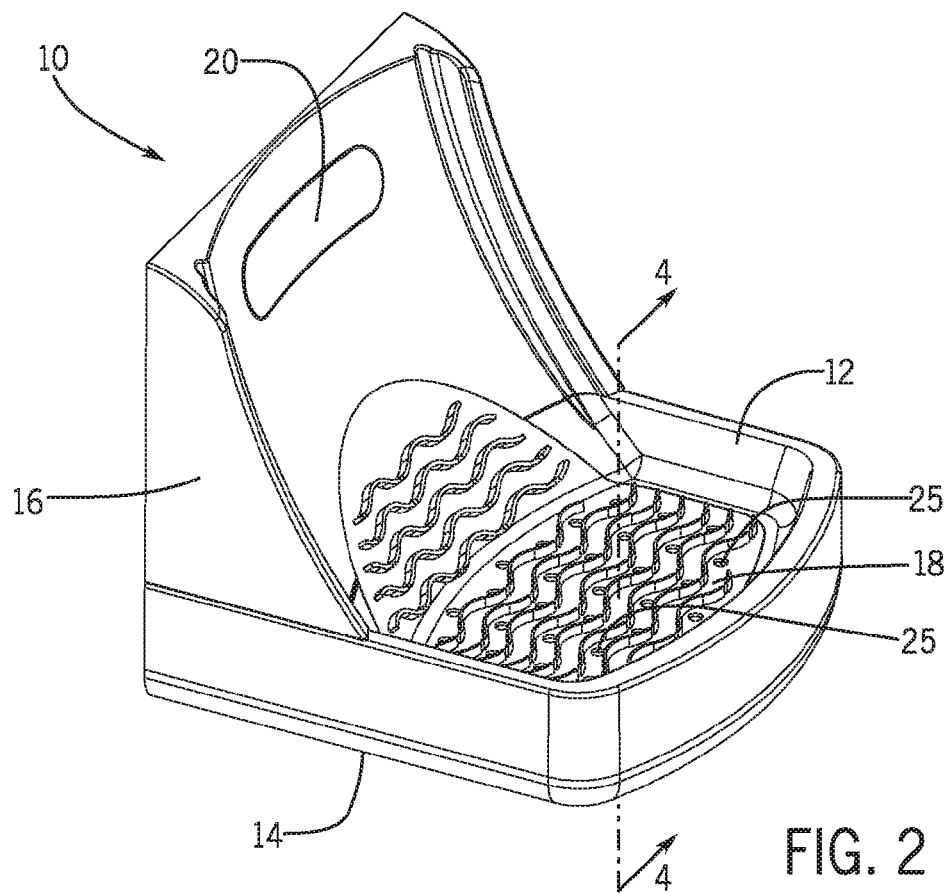
FIG. 2 is a perspective view of one embodiment of the present disclosure.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to catch drippings under a hand dryer while simultaneously deodorizing the surrounding area and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Catch Tray
2. Deodorizing Screen

The various elements of the device of the present disclosure may be related in the following exemplary fashion. It is not intended to limit the scope or nature of the relationships between the various elements and the following examples are presented as illustrative examples only.

By way of example, and referring to FIGS. 1-5, some embodiments of the present disclosure include a device for catching water under a hand dryer 11 while simultaneously deodorizing a surrounding area, the device comprising a catch tray 10 with a deodorizing screen 18, wherein when air from the hand dryer 11 hits the deodorizing screen 18, fragrance is released, deodorizing the surrounding area. In embodiments, the catch tray 10 may comprise a base tray 14 attached, such as removably attached, to a top tray 12; and a back wall 16 extending upward from the base tray 14, wherein the top tray 12 comprises a recessed sponge compartment 26 sized to accommodate a sponge 24. The deodorizing screen 18 may be removably secured or placed within the catch tray 10, such that it can be interchanged with replacement deodorizing screens 18. For example, the deodorizing screen 18 may include a flat portion with flow orifices 25 and an angled portion extending upward from the flat portion, wherein the angled portion may be positioned within a screen recess 28 in the back wall 16 and the flat portion may be positioned against the sponge 14, as shown in FIGS. 4 and 5. However, in other embodiments, the deodorizing screen 18 may have any shape and may be positioned anywhere on the catch tray 10. The catch tray 10 may further comprise a bracket 22 to mount the catch tray 10 to a vertical surface, such as a wall.

Figure 3:
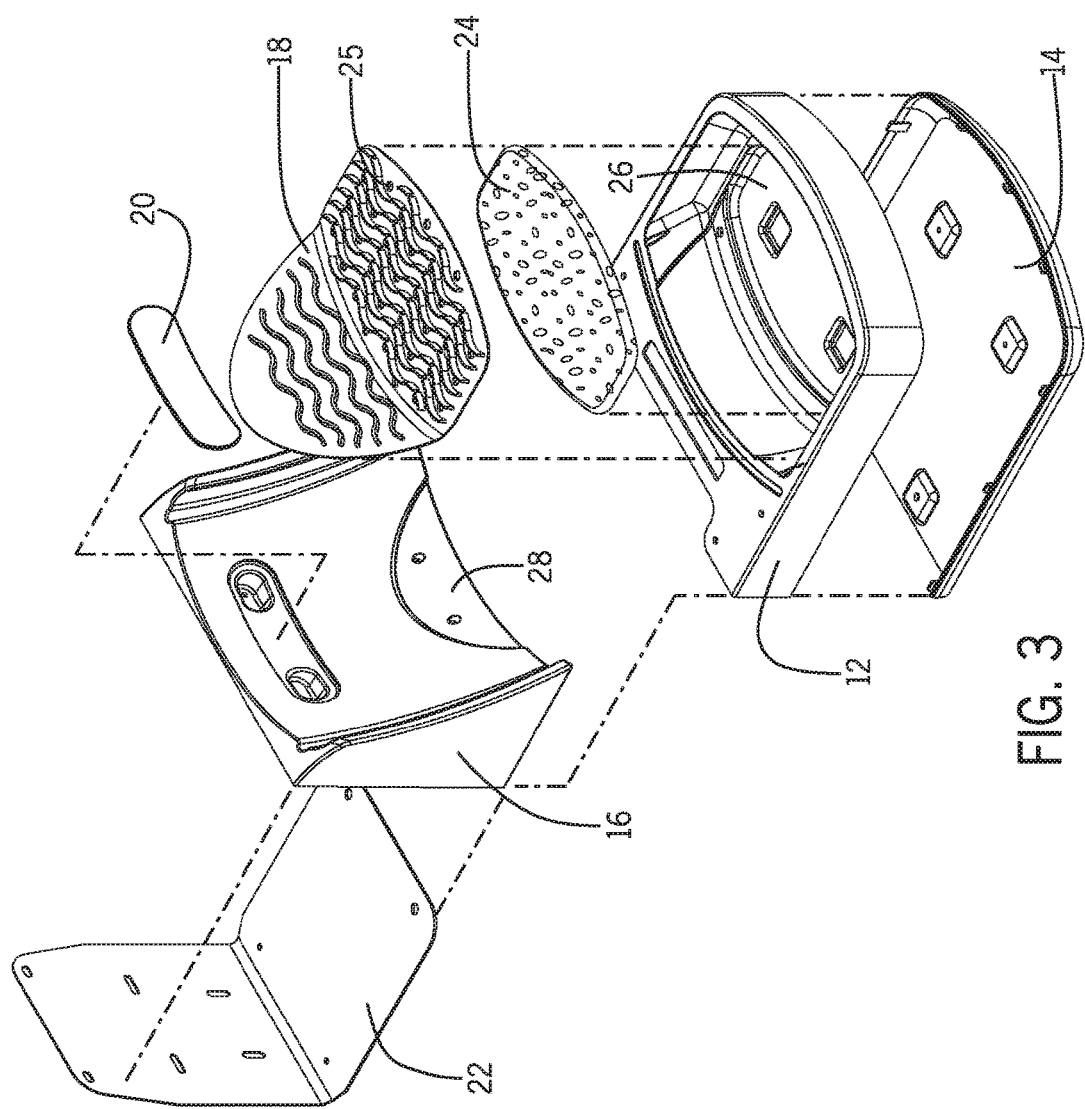
FIG. 3 is an exploded perspective view of one embodiment of the present disclosure.

As shown in the Figures, the base tray 14 and the top tray 12 may have substantially identical footprints, such that the base tray 14 is attached to a bottom surface of the top tray 12. In embodiments, the bracket 22 may be sandwiched between the base tray 14 and the top tray 12, such that the bottom of the L-shape is sandwiched and the vertical part of the L-shape is positioned against a back surface of the back wall 16, as shown in FIG. 3.

As mentioned above, the back wall 16 may extend upwards from the top tray 12 and the base tray 14, such as at about a 90° angle. A surface of the back wall 16 facing the base tray 14 may be slanted and, optionally, concavely curved. Thus, the back wall 16 may taper from a larger width proximate to the base tray 14 to a smaller width distal from the base tray 14. In some embodiments, the back wall 16 may thus be substantially chute-shaped. The shape of the back wall 16 may help water droplets coming from a user's hands to flow down into the top tray 12 and, specifically, into the sponge 24. The back wall 16 may optionally further comprise a logo plate 20 attached thereto, wherein the logo plate 20 could be used, for example, for marketing purposes.

As described above, the deodorizing screen 18 may removably engage with the catch tray 10, such as with the back wall 16 and the top tray 12. In embodiments, at least a portion of the deodorizing screen 18, such as the portion of the deodorizing screen designed to be positioned adjacent to the sponge 24, may comprise a plurality of flow orifices 25. The flow orifices 25 may serve multiple purposes. For example, the flow orifices 25 may both (1) allow water to flow therethrough onto the sponge 24, preventing or reducing spillage of water from the catch tray 10 and (2) allow air to flow therethrough, causing fragrance to be released. As shown in the Figures, the deodorizing screen 18 may also include decorative features, such as ridges extending across a surface facing away from the back wall 16 and the sponge 24.

The catch tray 10 of the present disclosure may be sized to be positioned under a hand dryer 11 and effectively catch water dripping from a user's hands while the user is drying his or her hands with the hand dryer 11, thus reducing spillage and drippage of water onto the floor and walls in the area surrounding the hand dryer 11. As shown in FIG. 1, the catch tray 10 may not be physically attached to the hand dryer 11 and, thus, may be used with any number of hand dryers 11 that currently exist. Alternatively, the catch tray 10 may be built into a hand dryer such that the hand dryer has a built-in catch tray with a deodorizing screen (not shown).

The catch tray 10 of the present disclosure may be made from any suitable materials. In some embodiments, the base tray 14, the top tray 12, and the back wall 16 may be made using plastic injection molding. Thus, the catch tray 10 may comprise a hard plastic material. The bracket 22 may comprise any suitable rigid material, such as galvanized metal and, thus, may give the catch tray 10 strength and rigidity while also allowing it to be mounted to a wall. The sponge 24 may comprise any conventional sponge material and may be easily removed for replacement. The deodorizing screen 18 may be made from any deodorizing material that, when hit with air from the hand dryer 11, may disperse a fragrance into the surrounding area. While the deodorizing screen 18 may constantly disperse a small amount of fragrance even when not being hit with air, due to the force of the air from the hand dryer 11, the deodorizing effect may be more powerful and effective when the hand dryer 11 is in use. The deodorizing screen 18 may be in the form of a replaceable insert such that, if and when the deodorizing screen 18 loses its strength, it may be easily replaced with a new deodorizing screen 18.

To use the catch tray 10 of the present disclosure, is may simply be mounted to the wall vertically below a hand dryer 11. When user dries his or her hands using the hand dryer 11, the forced air from the hand dryer 11 may hit the deodorizing screen 18, causing fragrance to be dispersed, while the catch tray 10 is simultaneously catching water droplets from the user's hands.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A device for catching water drippings below a hand dryer, comprising:
    a catch tray adapted to mount to a wall, the catch tray defining a recess in a top surface thereof, the catch tray including a base tray and a back wall, wherein a first recess portion is disposed in a top surface of the base tray and a second recess portion, continuous with the first recess portion, is disposed in an angled front face of the back wall;
    a deodorizing screen removably disposed in the recess, the deodorizing screen comprising a first screen portion disposed in the first recess portion and a second screen portion, at an angle to the first screen portion and continuous therewith, disposed in the second recess portion; and
    a sponge disposed in the recess below the first screen portion;
    wherein the catch tray does not include a cover such that the deodorizing screen is at all times exposed and visible from above the catch tray.

2. The device of claim 1, wherein the front face of the back wall slopes downward in a direction of the first recess portion defined in the top surface of the base tray.

3. The device of claim 1, wherein the back wall tapers from a larger width proximate the base tray to a smaller width distal from the base tray.

4. The device of claim 1, wherein the back wall is shaped such that water drippings contacting the front face of the back wall are directed toward the first recess portion defined in the top surface of the base tray.

5. The device of claim 1, wherein the deodorizing screen comprises a plurality of flow orifices through the first screen portion, and a plurality of ridges extending across a top face of each of the first and second screen portions.

6. The device of claim 1, further comprising a bracket adapted to mount the catch tray to a wall at a position below and spaced apart from a hand dryer.

\* \* \* \* \*